US009017352B2

(12) United States Patent
Plassman

(10) Patent No.: US 9,017,352 B2
(45) Date of Patent: Apr. 28, 2015

(54) HELICAL FIBRIN REMOVAL TOOL

(71) Applicant: Cook Medical Technologies LLC, Bloomington, IN (US)

(72) Inventor: Trevor Plassman, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 72 days.

(21) Appl. No.: 13/761,248

(22) Filed: Feb. 7, 2013

(65) Prior Publication Data

US 2014/0107678 A1    Apr. 17, 2014

Related U.S. Application Data

(63) Continuation-in-part of application No. 13/650,205, filed on Oct. 12, 2012, now Pat. No. 8,920,451.

(51) Int. Cl.
*A61B 17/3207* (2006.01)
*A61B 17/00* (2006.01)
*A61B 17/22* (2006.01)

(52) U.S. Cl.
CPC ..... *A61B 17/320758* (2013.01); *A61B 17/3207* (2013.01); *A61B 2017/00685* (2013.01); *A61B 2017/22034* (2013.01)

(58) Field of Classification Search
CPC .... A61B 17/3207; A61B 17/28; A61B 17/29; A61B 17/064
USPC ........ 606/159, 191, 200, 205–209, 127, 128, 606/114, 170, 172, 179, 180; 604/22; 600/562, 563, 564, 565, 567, 568, 569, 600/570, 571, 572
See application file for complete search history.

(56) References Cited

U.S. PATENT DOCUMENTS

| | | | | | |
|---|---|---|---|---|---|
| 3,683,891 | A | * | 8/1972 | Eskridge et al. | 600/564 |
| 3,749,085 | A | * | 7/1973 | Willson et al. | 600/570 |
| 4,030,503 | A | * | 6/1977 | Clark, III | 606/159 |
| 4,653,496 | A | * | 3/1987 | Bundy et al. | 606/159 |
| 4,706,671 | A | * | 11/1987 | Weinrib | 606/159 |
| 4,728,319 | A | * | 3/1988 | Masch | 604/22 |
| 4,890,611 | A | * | 1/1990 | Monfort et al. | 606/159 |
| 4,935,025 | A | * | 6/1990 | Bundy et al. | 606/180 |
| 5,007,896 | A | * | 4/1991 | Shiber | 604/22 |
| 5,551,427 | A | * | 9/1996 | Altman | 600/374 |
| 6,083,237 | A | * | 7/2000 | Huitema et al. | 606/180 |
| 6,156,046 | A | * | 12/2000 | Passafaro et al. | 606/159 |
| 6,165,187 | A | * | 12/2000 | Reger | 606/159 |
| 6,824,545 | B2 | * | 11/2004 | Sepetka et al. | 606/113 |

(Continued)

*Primary Examiner* — Jonathan W Miles
*Assistant Examiner* — George J Ulsh
(74) *Attorney, Agent, or Firm* — Brinks Gilson & Lione

(57) ABSTRACT

A fibrin removal assembly includes a single helical coil with a plurality of windings. A plurality of cutting elements extends from the windings into the lumen of the coil. Each of the cutting elements has a cutting edge, and all cutting edges point in a blade direction relative to a circumferential direction that promotes a penetration of tissue by the cutting elements in a cutting direction about the longitudinal axis and evading in a rotational direction opposite to the cutting direction. The cutting elements may further have a dull edge acting as radially inward ramps for tissue during a rotation in the second rotational direction. The windings may be wound in a direction that translates into a proximal movement of the coil when the coil is rotated in the cutting direction and into a distal movement when the coil is rotated opposite to the cutting direction.

15 Claims, 3 Drawing Sheets

(56) References Cited

U.S. PATENT DOCUMENTS

| | | | |
|---|---|---|---|
| 7,806,871 B2* | 10/2010 | Li et al. | 604/164.06 |
| 8,123,769 B2* | 2/2012 | Osborne | 606/159 |
| 8,246,641 B2* | 8/2012 | Osborne et al. | 606/159 |
| 2002/0183733 A1* | 12/2002 | Mulier et al. | 606/28 |
| 2007/0005084 A1* | 1/2007 | Clague et al. | 606/159 |
| 2010/0274266 A1* | 10/2010 | Rimer et al. | 606/151 |
| 2012/0109171 A1* | 5/2012 | Zeroni et al. | 606/159 |

* cited by examiner

HELICAL FIBRIN REMOVAL TOOL

CROSS-REFERENCE TO RELATED APPLICATION

The present application is a Continuation-in-Part of U.S. patent application Ser. No. 13/650,205, filed on Oct. 12, 2012, entitled "DEVICE AND METHOD FOR REMOVING TISSUE INSIDE A BODY VESSEL," incorporated herein in its entirety by reference.

TECHNICAL FIELD

The present application relates to a device and a method for removing tissue inside a body vessel. More specifically, the application relates to a fibrin removal tool and a method of removing fibrin from a body vessel.

BACKGROUND

When a blood clot forms in a venous vessel and is left in the vessel for more than about two weeks, it starts forming fibrin strands, so-called synechiae. The fibrin strands do not only contribute to an obstruction of the vessel, but also thicken the vessel walls and thus limit the elasticity of the vessel walls.

It is known to reopen a body vessel by implanting a stent that presses the fibrin strands against the vessel wall. It is further known to remove fibrin strands from vessel walls with fairly complex tools.

SUMMARY

According to one aspect of the invention, a fibrin removal assembly comprises a single helical coil with a plurality of windings defining a longitudinal lumen with a central longitudinal axis. A plurality of cutting elements extends from the windings into the lumen. Each of the cutting elements has a cutting edge that points in a blade direction relative to a circumferential direction that promotes a penetration of tissue by the cutting elements in a cutting direction about the longitudinal axis. By arranging the cutting elements on the inside of the coil, the risk of inadvertently cutting into a vessel wall surrounding the coil is significantly reduced. Further, by providing one rotational cutting direction, the process of cutting fibrin strand or other tissue can be fairly accurately controlled by rotating the coil.

According to another aspect of the invention, the cutting elements further have a dull edge acting as radially inward ramps for tissue during a rotation in the second rotational direction. This arrangement provides that during a rotation opposite to the cutting direction, the tissue inside the coil lumen is not penetrated by the cutting edges.

According to a further aspect of the invention, the windings are wound in a direction that translates into a proximal movement of the coil when the coil is rotated in the first rotational direction and into a distal movement of the coil when the coil is rotated in the second rotational direction. Thus, a rotation in the second rotational direction allows for a precise distal placement of the coil inside the body vessel, while a rotation in the cutting direction severs tissue in the path of the cutting edges, while simultaneously moving the coil in a proximal direction.

According to yet another aspect of the invention, the cutting elements reside in an axial portion of the helical coil where they occupy a position radially extending into the lumen at least as far as any other part of the helical coil in the axial portion. This position of the cutting elements promoted engagement of the cutting elements with tissue present in the lumen of the coil.

According to another aspect of the invention, at least a portion of the cutting edges extends in a direction generally parallel to the longitudinal axis. This alignment primarily promotes cutting of tissue extending in a generally radial direction.

According to a further aspect of the invention, at least a portion of the cutting edges extends in a generally radial direction, thereby promoting cutting of tissue extending in a generally axial direction.

According to yet another aspect of the invention, the windings of the coil have an axial thickness and a pitch, the pitch being at least twice as large as the axial thickness, preferably at least about three times as large as the axial thickness. Such a spacing allows fibrin tissue to extend through the spaces between the coil windings. For example, the coil may be rotated to drill itself along the lumen of the body vessel. When the distal end of the coil is moved between a fibrin strand and the vessel wall, the fibrin strand can travel along the coil windings until the coil has reached a position in which a rotation in the cutting direction is intended. While the coil windings have penetrated the fibrin strands, the fibrin strands extend from the vessel wall into the lumen of the coil through the spaces between the coil windings.

According to another aspect of the invention, the cutting elements are unitarily formed by undercuts formed in the windings. Such undercuts are easy to manufacture by longitudinally introducing a cutting tool into the lumen of the coil and moving the tool at an intended angle into the interior surfaces of the windings, thus forming the undercuts.

According to a further aspect of the invention, the fibrin removal assembly further comprises an elongated guide member with a distal end connected to a proximal end of the coil and a proximal end with a handle configured for rotating the coil about the longitudinal axis. Thus, the coil can be rotated remotely from the proximal end of the elongated guide member by hand or by an appropriate drive, such as a rotary motor.

One preferred manner of attaching the coil to the elongated guide member involves windings with a reduced diameter at the proximal end of the coil. The windings may embrace the distal end of the elongated guide member for a positive lock.

According to yet another aspect of the invention, the fibrin removal assembly may further comprise a catheter dimensioned to have a diameter large enough to accommodate the coil. The elongated guide member is preferably at least as long as the catheter.

According to another aspect of the invention, a method of removing tissue from a tissue site in a body vessel is provided. The method comprises a first step of providing a single helical coil having a plurality of windings defining a longitudinal lumen with a central longitudinal axis, a plurality cutting elements extending from the windings into the lumen, each of the cutting elements having a cutting edge, all cutting edges pointing in a blade direction relative to an circumferential direction, the blade direction promoting a penetration of tissue by the cutting elements in first rotational direction about the longitudinal axis being a cutting direction and not in second rotational direction about the longitudinal axis opposite the cutting direction, the coil being attached to an elongated guide member having a proximal rotating handle. Further, a catheter with a lumen of a diameter large enough to accommodate the helical coil is provided. A distal end of the catheter is distally inserted into the body vessel to a position proximate to and proximal from the tissue site. Then, the helical coil is distally moved with the elongated guide member to a position near the distal end of the catheter and further until the coil overlaps at least partially with the tissue site. Tissue residing in the coil lumen is then cut by rotating the rotating handle in the first rotational direction. Subsequently, the coil can be proximally removed.

According to a further aspect of the invention, if the windings are wound in a direction that causes a distal movement of the coil when the coil is rotated in the second rotational direction, the helical coil can be distally moved to overlap with the tissue site by rotating the rotating handle in the second rotational direction.

Further details and benefits of the invention become apparent from the following description of preferred embodiments shown in the accompanying drawings. The drawings are provided for purely illustrative purposes and are not intended to limit the scope of the present invention.

DETAILED DESCRIPTION OF THE DRAWINGS

When a blood clot forms in a venous vessel and is left in the vessel for more than about two weeks, it starts forming fibrin strands, so-called synechiae. The fibrin strands do not only contribute to an obstruction of the vessel, but also thicken the vessel walls and thus limit the elasticity of the vessel walls. Thus, the present invention provides a safe way of reopening the vessel by removing fibrin strands while reducing the risk of injury to the vessel walls.

Figure 1:
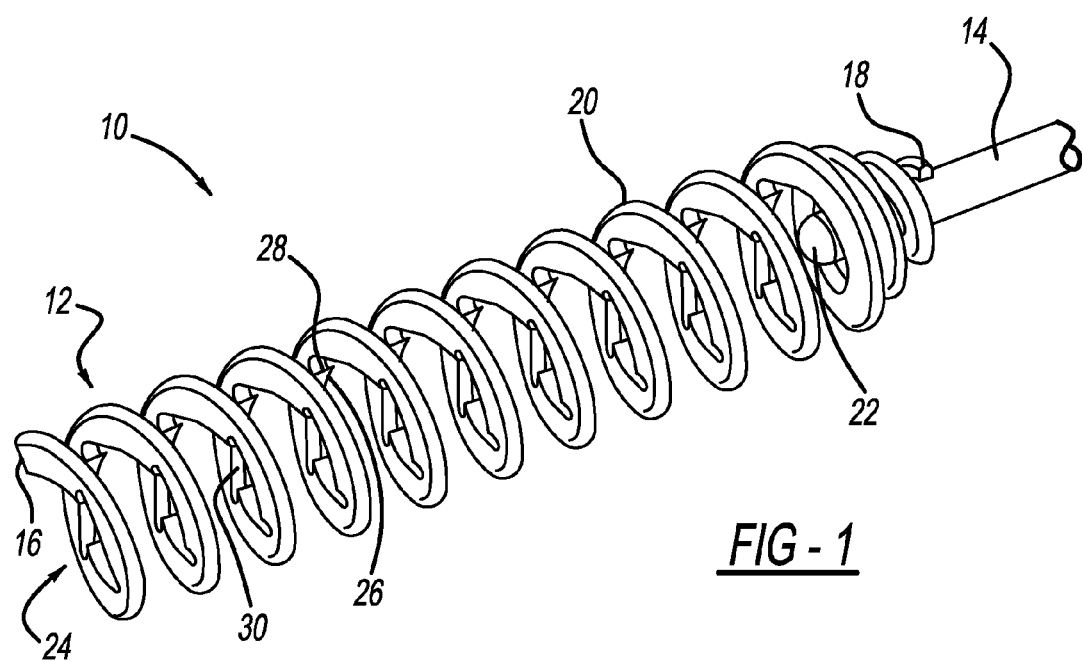
FIG. 1 shows a perspective view of a first embodiment of a helical fibrin removal tool according to the present invention.
Figure 2:
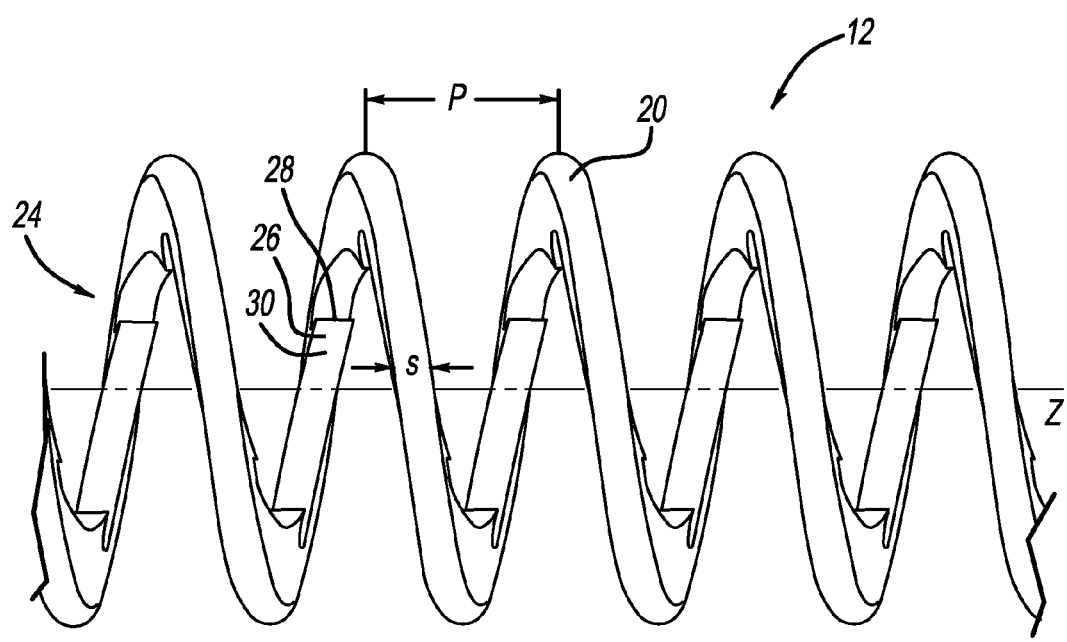
FIG. 2 shows a first partial view of the helical fibrin removal tool of FIG. 1.
Figure 3:
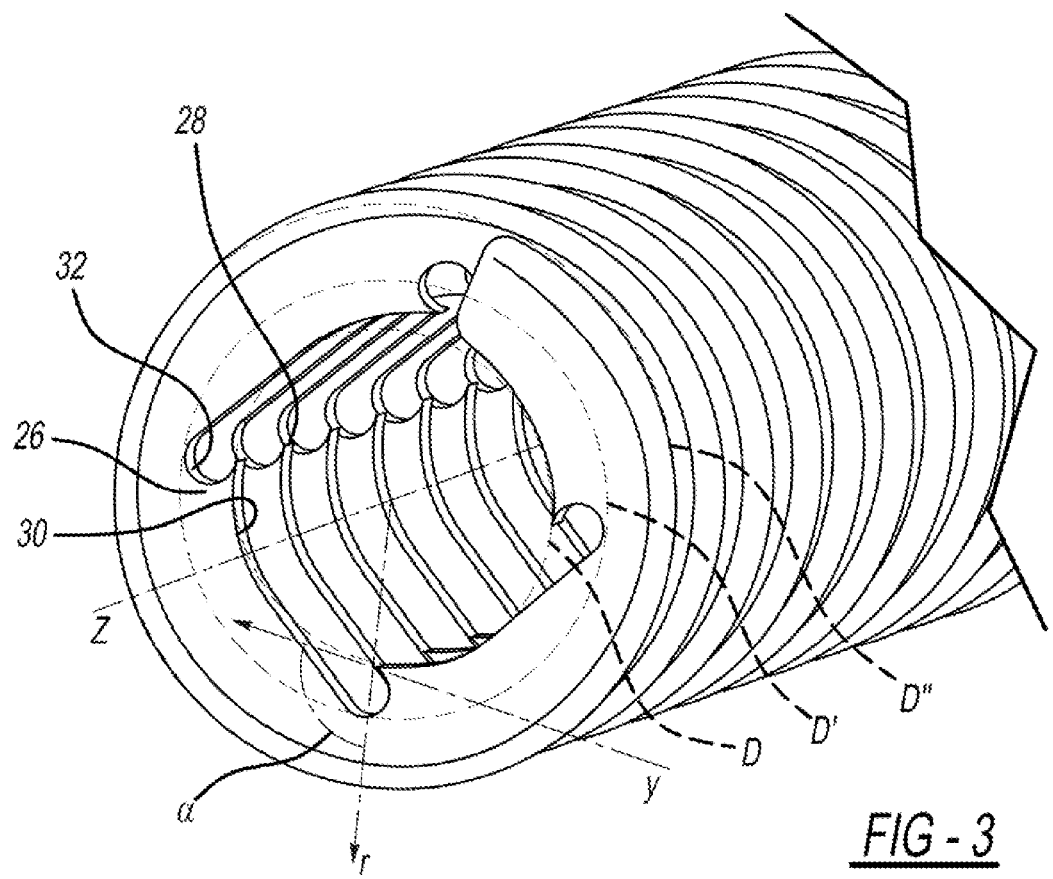
FIG. 3 shows a second partial view of the helical fibrin removal tool of FIG. 1

Now referring to FIGS. 1 through 3, a fibrin removal tool 10 comprises a helical coil 12 and an elongated guide member 14, such as a guide wire guide. The helical coil 12 is wound in a direction corresponding to a corkscrew. This means that a clockwise twist from one end will drill the other end of the coil 12 into tissue in a screw-like movement, while a counterclockwise turn will withdraw the coil from the tissue. In this context, a screw-like movement is a rotation about a longitudinal axis Z with a superimposed axial movement proportional to the degrees of rotation. While corkscrew windings are shown, opposite windings are well within the scope of the invention, where a counterclockwise turn effects a screw-like penetration and a clockwise turn a withdrawal.

The coil 12 of FIG. 1 is formed from a flattened wire with a greater radial thickness x than axial thickness s. This detail is more clearly visible in FIG. 2 that shows a radial view of a detail of the coil 12 of FIG. 1. FIG. 2 illustrates that the radial thickness x is about equal to or greater than the axial thickness s.

Now referring to FIG. 1 again, the coil 12 has a distal end 16 with rounded edges to avoid injuries of a vessel wall when inserted into a body vessel. The coil 12 further has a proximal end 18 with windings 20 narrowing toward the proximal end so as to secure a distal end 22 of the elongated guide member 14. The distal end 22 of the elongated guide member may have radial protrusions to form a positive lock with the windings 20 of the coil. Alternatively or additionally, the coil may be held on the elongated guide member 14 by friction, solder, or adhesive.

Preferably, the coil 12 has a relaxed shape that provides a sufficient gap between individual windings 20 to allow for a radial ingress of fibrin tissue from the vessel wall into the lumen 24 of the coil 12. The term "relaxed state" in this context means a shape that the coil adopts without the influence of external forces. The gap between windings 20 is determined by the pitch P of the coil 12 and the axial thickness of the windings 20, where the pitch P is the axial distance by which the coil propagates in one 360° turn as shown in FIG. 2. The pitch P is preferably chosen to be at least three times the axial thickness s. In the embodiment shown, the pitch measures about five times the axial thickness s.

As best visible in FIG. 3, the helical coil 12 has an axial portion with a substantially constant outer diameter D", in which a set of cutting elements 26 is arranged on the inside of the coil windings 20. The cutting elements 26 point generally inward into the lumen of the first helical coil 12. As visible in FIG. 2, the cutting elements 26 are arranged in a way that a cutting edge 28 extends generally parallel to the longitudinal axis Z. In other words, apart from the proximal end 18 fastened to the elongated guide member 14, none of the coil material radially protrudes farther into the coil lumen 24 than the cutting edges 28 of the cutting elements 26. Further, as evident from FIG. 3, each axially extending cutting edge 28 points into an angular blade direction y that forms an obtuse angle α with a radial direction r.

In the embodiment shown in FIGS. 1 through 3, in which the coil 12 is wound like a corkscrew, the cutting edges 28 are preferably active in the rotational direction of withdrawal of the coil 12. Thus, if viewed from the proximal end 18 of the coil 12, a counterclockwise rotation of the coil in withdrawal direction causes the cutting elements 26 to move in their cutting direction and to cut any tissue residing in the path of the cutting edges 28. Conversely, a clockwise rotation in the drilling direction causes any tissue inside the lumen 24 of the coil 12 to slide along interior flattened or dull edges 30 of the cutting elements 26. Thus the dull edges 30 operate like ramps rendering the cutting edges 28 inactive.

In the embodiments shown, the cutting elements 26 are formed unitarily with the coil 12. As illustrated in FIG. 3, this can be accomplished, for example, by removing material on the inside of the coil 12. Initially, the coil 12 has an small inner diameter D indicated by a first broken line. A milling tool may be axially inserted into the coil 12 before assembly to produce circumferential undercuts 32. For example, in the embodiment shown in FIG. 3, the undercuts 32 collectively form axially extending grooves on the inside of the coil 12 each of which is arranged at an oblique angle relative to the radial direction r, resulting in cutting elements with a profile defined on one side by the inner circumferential edge of the coil 12 extending generally along the inner diameter D of the coil 12 that forms the dull edges 30 and on the other side by the outer oblique edge of the undercut 32. Thus, each cutting element 26 forms a wedge protruding into the lumen of the coil 12, where the intersection of the dull edge 30 with the oblique edge of the undercut 32 forms the cutting edge 28 pointing in the blade direction y that form the obtuse angle α relative to the radial direction r. The undercuts 32 extend radially to an intermediate diameter D' that is greater than the inner diameter D and smaller than the outer diameter D" of the coil 12.

While the embodiment shows cutting elements 26 unitary with the coil 12, the cutting elements 26 may also be attached to the inside of the coil 12 by soldering or other suitable methods. Where the cutting elements 26 are attached to the inside of the coil 12, the diameter of the coil 12 may correspond to the intermediate diameter D' and the cutting elements extend inward to a radial position corresponding to the small interior diameter D.

Figure 4:
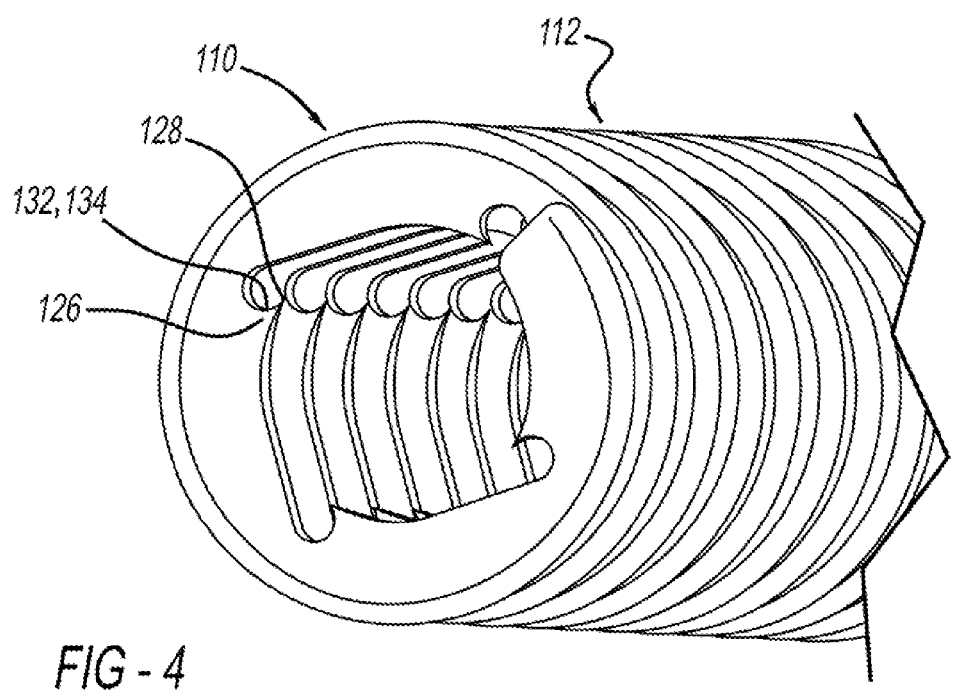
FIG. 4 shows a partial view of a second embodiment of a helical fibrin removal tool according to the present invention.

FIG. 4 shows a variation in a fibrin removal tool 110 with a coil 112, in which cutting tips 128 of cutting elements 126 do not extend in an axial direction, but are generally point-shaped. Instead, a portion of the undercut 132 that extends from the inner diameter D to the intermediate diameter D' may form a sharpened blade 134 that extends in a generally radial direction r. The term "generally radial direction" is used in a sense that opposite ends of the blade 134 are radially offset from each other. A portion of the blade 134 itself or the entire blade 134 may optionally also extend along the radial direction r. The different orientations of the blades 134 compared to the cutting edges 28 of FIGS. 1-3 provide that the blades primarily cut material that extend longitudinally, while the cutting edges 28 primarily severs material extending in the radial direction.

It is well within the scope of the present invention to provide a coil that carries cutting elements 26 and cutting elements 126. Further, cutting elements may be hybrids between the cutting elements 26 and the cutting elements 126 and include both an axially extending cutting edge 28 and a generally extending cutting blade 134 without leaving the scope of the present invention.

While the drawings depict helical coils 12 and 112 with four angular locations around the circumference, on which cutting elements 26 or 126 are placed, the number of angular positions is variable. Further, not every single one of the windings 20 needs to carry cutting elements. For example, coils carrying generally radially extending cutting blades, such as cutting blades 134, may provide a greater axial distance between cutting blades in identical angular positions.

In a further variation, the coil may have a changing outer diameter D" so that the coil has a cone-like or bulbous shape. The cutting elements 26 then extend to an axially local small diameter D that changes with the local outer diameters D". Thus, in each axial portion of the helical coil containing cutting elements, the cutting elements occupy a position, in which they radially protrude into the lumen at least as far as any other portion of the helical coil in that axial portion.

Suitable materials for the coil 12 and for the cutting elements 26 and 126 of the various embodiments include stainless steel and austenic nickel-chromium-based super alloys, such as Inconel. The elongated guide member 14 may be a customary guide wire or narrow tube. The outside dimensions of the fibrin removal tools 10 and 110 can be adapted to the diameter of the body vessel, into which the fibrin removal tool 10 or 110 is to be inserted. This allows cutting of fibrin strands close to the vessel wall and without the prior insertion of an implant protecting the vessel walls. The coil 12 or 112 can then be screwed into the body vessel until the cutting elements 26 and 126 are properly aligned for cutting. By subsequently "unscrewing" the coil, the cutting elements 26 and 126 are moved in their cutting directions for severing material located in the lumen of the coil 12 or 112.

To reduce adherence of the outside of the fibrin removal device to the vessel walls and to the tissue, coatings may be applied before assembly. One suitable coating is, for example, PTFE.

Figure 5:
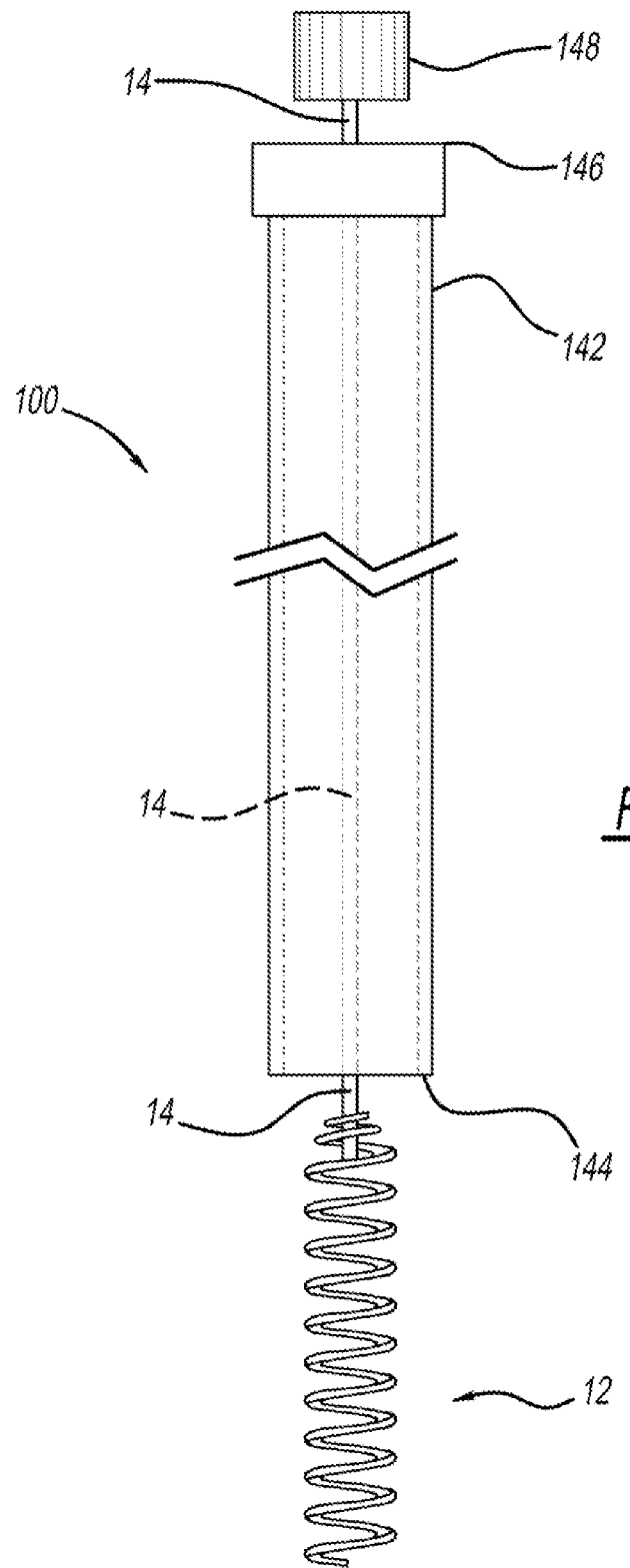
FIG. 5 shows a helical fibrin removal tool assembly including a catheter.

FIG. 5 shows an example of a fibrin removal assembly 100 with the fibrin removal tool 110. The following description is equally applicable to a fibrin removal assembly including a different fibrin removal tool according to any one of the preceding figures or a modification thereof. FIG. 5 only shows relevant proximal and distal portions of the fibrin removal assembly 100. Between the distal and proximal portions, an additional length is added depending on the circumstances of use, such as the fibrin location inside the patient body and the access path.

The fibrin removal assembly 100 has a sheath or catheter 142 that is initially inserted into a body vessel in a known manner, for example along a guide wire or through an outer catheter that has previously been introduced. The elongated guide member 14 of the fibrin removal tool 10 is introduced into the catheter 142 from the proximal end 146 of the catheter 142 to the distal end 144 of the catheter 142 through the lumen of the catheter 142. The elongated guide member is preferably stiff enough to allow pushing of the coil 12 to the distal end 144. Once the coil 12 has generally reached the distal end of the catheter 142, a further distal movement of the coil may be accomplished by rotating The coil 12 can be rotated about the longitudinal axis Z with a rotating handle 148 positioned at the proximal end of the elongated guide member, proximal of the proximal end 146 of the catheter 142. For a screw-type coil 12 as shown in FIG. 5, a clockwise rotation of the rotating handle 148 drills the coil 12 proximally into tissue. A subsequent counter-clockwise rotation causes the cutting elements 26 to cut tissue residing in the path of the cutting edges 28 or, if a different removal tool is chosen, in the path of the cutting blades 134. For allowing the coil 12 to distally move past the distal end 144 of the catheter 142, the elongated guide member 14 is preferably at least about as long as the catheter 142 that is paired with the coil 12.

Because all cutting edges 28 and cutting blades 134 are located inside the lumen of the coil 12 and because the distal end of the coil is rounded or dull, any risk of unintended injury to vessel walls is greatly reduced. Any material cut by the cutting elements 26 or 126 remains generally inside the coil 12 or 112 and can be distally moved from the vessel with the coil. Once the coil is retracted to be entirely or mostly surrounded by the catheter 142, the catheter can be safely removed with the coil 12 or 112. Alternatively, the coil may be proximally removed from the catheter 142, for example, in the event that further procedures are planned involving a use of the catheter 142. Optionally, the catheter 142 may be connected to a suction device generally known in the art.

The rotating handle 148 may be manipulated manually or may be attached to a suitable motor that is not depicted in FIG. 5.

While the foregoing description made reference to fibrin strands and cutting thereof, the invention is not limited to such a use and is suited for taking biopsy samples or for any cutting of intravascular tissue with a reduced risk of damaging the vessel wall.

The foregoing description of various embodiments of the invention has been presented for purposes of illustration and description. It is not intended to be exhaustive or to limit the invention to the precise embodiments disclosed. Numerous modifications or variations are possible in light of the above teachings, and the properties of one embodiment may be modified with properties of another. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A fibrin removal assembly comprising:
    a single helical coil having a plurality of windings defining a longitudinal lumen with a central longitudinal axis, and
    a plurality of cutting elements formed in one piece with the helical coil and extending from the windings into the lumen, each of the cutting elements having a cutting edge extending into the lumen, all cutting edges pointing in a blade direction relative to an circumferential direction, the blade direction promoting a penetration of tissue by the cutting elements in a first rotational direction about the longitudinal axis being a cutting direction and evading penetration in a second rotational direction about the longitudinal axis opposite the cutting direction.

2. The fibrin removal assembly of claim 1, wherein the cutting elements further have a dull edge acting as radially inward ramps urging tissue into the lumen during a rotation in the second rotational direction.

3. The fibrin removal assembly of claim 1, wherein the windings are wound in a direction that translates into a proximal movement of the coil when the coil is rotated in the first rotational direction and into a distal movement of the coil when the coil is rotated in the second rotational direction.

4. The fibrin removal assembly of claim 1,
    wherein the cutting elements reside in an axial portion of the helical coil where the cutting edges occupy a position radially extending into the lumen at least as far as any other part of the helical coil in the axial portion.

5. The fibrin removal assembly of claim 1,
    wherein the cutting edges extend in a direction generally parallel to the longitudinal axis.

6. The fibrin removal assembly of claim 1,
    wherein the cutting edges extend in a generally radial direction.

7. The fibrin removal assembly of claim 1,
    wherein the windings of the coil have an axial thickness and a pitch, the pitch being at least twice as large as the axial thickness.

8. The fibrin removal assembly of claim 7,
wherein the pitch is at least about three times as large as the axial thickness.

9. The fibrin removal assembly of claim 1,
    wherein the cutting elements are unitarily formed by axially extending grooves in the windings.

10. The fibrin removal assembly of claim 1, further comprising an elongated guide member having a distal end connected to a proximal end of the coil and a proximal end with a handle configured for rotating the coil about the longitudinal axis.

11. The fibrin removal assembly of claim 10,
    wherein the proximal end of the coil has windings with a reduced diameter embracing the distal end of the elongated guide member.

12. The fibrin removal assembly of claim 10, further comprising a catheter having a catheter lumen dimensioned to have a diameter large enough to accommodate the coil.

13. The fibrin removal assembly of claim 10, wherein the elongated guide member is at least as long as the catheter.

14. A method of removing tissue from a tissue site in a body vessel, the method comprising the following steps:
    providing a single helical coil having a plurality of windings defining a longitudinal lumen with a central longitudinal axis, a plurality cutting elements formed in one piece with the helical coil and extending from the windings into the lumen, each of the cutting elements having a cutting edge extending into the lumen, all cutting edges pointing in a blade direction relative to an circumferential direction, the blade direction promoting a penetration of tissue by the cutting elements in first rotational direction about the longitudinal axis being a cutting direction and not in second rotational direction about the longitudinal axis opposite the cutting direction, the coil being attached to an elongated guide member having a proximal rotating handle;
    providing a catheter with a lumen of a diameter large enough to accommodate the helical coil;
    distally inserting a distal end of the catheter into the body vessel to a position proximate to and proximal from the tissue site;
    distally moving the helical coil with the elongated guide member to a position near the distal end of the catheter;
    distally moving the helical coil until the coil overlaps at least partially with the tissue site;
    rotating the rotating handle in the first rotational direction to cut tissue residing in the coil lumen; and
    proximally removing the coil.

15. The method of claim 14, wherein the windings are wound in a direction that causes a distal movement of the coil when the coil is rotated in the second rotational direction and wherein the helical coil is distally moved to overlap with the tissue site by rotating the rotating handle in the second rotational direction.

* * * * *